US010336981B2

(12) United States Patent
Ribbe et al.

(10) Patent No.: US 10,336,981 B2
(45) Date of Patent: Jul. 2, 2019

(54) RECOMBINANTLY ENGINEERED DIAZOTROPHS FOR WHOLE CELL HYDROCARBON PRODUCTION AND METHODS FOR MAKING AND USING THEM

(71) Applicant: The Regents of the University of California, Oakland, CA (US)

(72) Inventors: Markus Walter Ribbe, Irvine, CA (US); Yilin Hu, Irvine, CA (US); Johannes Rebelein, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/536,653

(22) PCT Filed: Dec. 17, 2015

(86) PCT No.: PCT/US2015/066481
§ 371 (c)(1),
(2) Date: Jun. 15, 2017

(87) PCT Pub. No.: WO2016/100727
PCT Pub. Date: Jun. 23, 2016

(65) Prior Publication Data
US 2017/0306291 A1   Oct. 26, 2017

Related U.S. Application Data

(60) Provisional application No. 62/093,955, filed on Dec. 18, 2014.

(51) Int. Cl.
| | |
|---|---|
| *C12Q 1/04* | (2006.01) |
| *C07K 14/21* | (2006.01) |
| *C12F 3/04* | (2006.01) |
| *C12N 1/20* | (2006.01) |
| *C12M 1/24* | (2006.01) |
| *C12P 3/00* | (2006.01) |
| *C12P 5/02* | (2006.01) |

(52) U.S. Cl.
CPC ............... *C12N 1/20* (2013.01); *C07K 14/21* (2013.01); *C12F 3/04* (2013.01); *C12M 23/08* (2013.01); *C12P 3/00* (2013.01); *C12P 5/02* (2013.01); *C12P 5/023* (2013.01); *C12P 5/026* (2013.01); *C12Q 1/04* (2013.01); *Y02E 50/343* (2013.01)

(58) Field of Classification Search
CPC ............. C12Q 1/04; C07K 14/21; C12N 1/20
USPC ..... 435/6.1, 91.1, 91.31, 455; 536/23.1, 24.5
See application file for complete search history.

(56) References Cited

U.S. PATENT DOCUMENTS 5,096,819 A * 3/1992 Page .................. C12P 7/625
435/135
2009/0042236 A1 2/2009 Bishop et al.

FOREIGN PATENT DOCUMENTS

EP    0339830 A2 *  11/1989  ........... C07K 14/195
EP    0339830 A2     11/1989

OTHER PUBLICATIONS

Mouncey et al, J. Bacteriology, vol. 177, No. 18, pp. 5294-5302. (Year: 1995).*
Bothe, Hermann, et al., "Nitrogen Fixation and Hydrogen Metabolism in Cyanbacteria", Microbiology and Molecular Biology Reviews, vol. 74, No. 4, (Dec. 2010), pp. 529-551.
Fisher, Karl, et al., "Azotobacter vinelandii Vanadium Nitrogenase: Formaldehyde is a Product of Catalyzed HCN Reduction and Excess Ammonia Arises Directly from Catalyzed Azide Reduction", Biochemistry, vol. 45, No. 13, Apr. 4, 2006, pp. 4190-4198.
Hernandez, Jose, A., et al., "Molybdenum Trafficking for Nitrogen Fixation", Biochemistry, vol. 48, No. 41, Oct. 20, 2009, pp. 9711-9721.
Mouncey, N.J., et al., "Mutational analysis of genes of the mod locus involved in molybdenum transport, homeostasis, and processing in Azotobacter vinelandi" J Bacteriol., vol. 177, No. 18, (Sep. 1995), pp. 5294-5302.
Copenheaver, Blaine, R., et al., "International Search Report", Patent Cooperation Treaty Application No. PCT/US2015/066481, United States of America as International Searching Authority, International Search Completed Feb. 22, 2016, International Search Report dated Mar. 4, 2016, (3 pages).

* cited by examiner

*Primary Examiner* — Jane J Zara
(74) *Attorney, Agent, or Firm* — Greer, Burns & Crain, LTD.; Gregory P. Einhorn

(57) ABSTRACT

In alternative embodiments, provided are genetically or recombinantly engineered nitrogen-fixing, nitrogenase expressing bacteria capable of enzymatically synthesizing hydrocarbons, and methods for making and using them. In alternative embodiments, provided are genetically or recombinantly engineered nitrogen-fixing, nitrogenase expressing bacteria including nitrogen-fixing diazotrophs such as nitrogen-fixing bacteria of the family Pseudomonadaceae, or the genus *Azotobacter*, for the whole cell synthesis of hydrocarbons and carbon-carbon bonds. In alternative embodiments, nitrogen-fixing, nitrogenase-expressing bacteria used to practice the invention are genetically or recombinantly engineered to express an exogenous nitrogenase express more endogenous nitrogenase or have increased nitrogenase, activity. In alternative embodiments, nitrogen-fixing, nitrogenase-expressing bacteria used to practice the invention are genetically or recombinantly engineered to lack or have decreased molybdenum transporter activity. In alternative embodiments, provided are culture systems, fermenters and bioreactors using nitrogen-fixing, nitrogenase-expressing bacteria for enzymatically synthesizing hydrocarbons.

18 Claims, 2 Drawing Sheets

Fig. 1

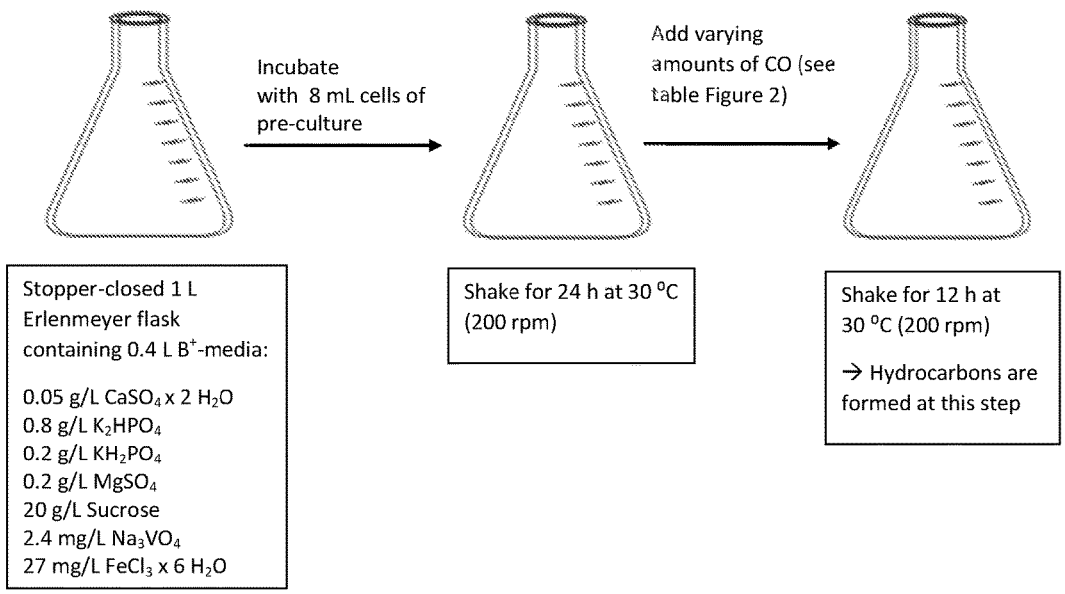

Stopper-closed 1 L Erlenmeyer flask containing 0.4 L B⁺-media:

0.05 g/L $CaSO_4 \times 2\ H_2O$
0.8 g/L $K_2HPO_4$
0.2 g/L $KH_2PO_4$
0.2 g/L $MgSO_4$
20 g/L Sucrose
2.4 mg/L $Na_3VO_4$
27 mg/L $FeCl_3 \times 6\ H_2O$ Shake for 24 h at 30 °C (200 rpm)

Shake for 12 h at 30 °C (200 rpm)

→ Hydrocarbons are formed at this step

Fig. 2A

| Product | Methane ($CH_4$) | Ethene ($C_2H_4$) | Ethane ($C_2H_6$) | Propane ($C_3H_8$) | Total |
|---|---|---|---|---|---|
| Amount of CO added (%) | (mol $CH_4$/ mol enzyme) | (mol $C_2H_4$/ mol enzyme) | (mol $C_2H_6$/ mol enzyme) | (mol $C_3H_8$/ mol enzyme) | Estimated total turnover per enzyme |
| 0 | 0 | 0 | 0 | 0 | 0 |
| 2 | 9.84 | 15.204 | 0.72 | 0 | 25.77 |
| 5 | 16.88 | 217.77 | 8.56 | 2.626 | 245.83 |
| 7.5 | 21.03 | 224.50 | 8.58 | 2.415 | 256.53 |
| 10 | 17.81 | 226.96 | 8.67 | 1.892 | 255.35 |
| 20 | 24.10 | 171.61 | 7.03 | 1.933 | 204.68 |
| 30 | 29.25 | 113.72 | 4.71 | 2.086 | 149.78 |
| 40 | 23.66 | 60.74 | 2.70 | 0.059 | 87.17 |
| 50 | 21.05 | 18.26 | 1.10 | 0.431 | 40.85 |

RECOMBINANTLY ENGINEERED DIAZOTROPHS FOR WHOLE CELL HYDROCARBON PRODUCTION AND METHODS FOR MAKING AND USING THEM

RELATED APPLICATIONS

This application is a national phase of International patent application serial number PCT/US2015/066481, filed Dec. 17, 2015, which claims benefit of priority to U.S. provisional application 62/093,955, filed Dec. 18, 2014. The contents of each of these applications are incorporated herein by reference in their entirety and for all purposes.

TECHNICAL FIELD

This invention generally relates to bacterial molecular and cellular biology, and biofuels. In alternative embodiments, provided are genetically or recombinantly engineered nitrogen-fixing, nitrogenase-expressing bacteria capable of enzymatically synthesizing hydrocarbons, and methods for making and using them. In alternative embodiments, provided are genetically or recombinantly engineered nitrogen-fixing, nitrogenase expressing bacteria including nitrogen-fixing diazotrophs such as nitrogen-fixing bacteria of the family Pseudomonadaceae, or the genus *Azotobacter*, including *Azotobacter vinelandii*, for the whole cell synthesis of hydrocarbons and carbon-carbon bonds. In alternative embodiments, nitrogen-fixing, nitrogenase-expressing (such as vanadium nitrogenase-expressing) bacteria used to practice embodiments as provided herein are genetically or recombinantly engineered to express an exogenous nitrogenase, e.g., vanadium nitrogenase, express more endogenous nitrogenase, e.g., vanadium nitrogenase, or have increased nitrogenase, e.g., vanadium nitrogenase, activity. In alternative embodiments, nitrogen-fixing, nitrogenase-expressing bacteria used to practice embodiments as provided herein are genetically or recombinantly engineered to lack or have decreased molybdenum transporter activity, for example, by deletion of molybdenum transporter genes or inhibition of molybdenum transporter expression. In alternative embodiments, provided are culture systems and bioreactors using nitrogen-fixing, nitrogenase-expressing bacteria provided herein for enzymatically synthesizing hydrocarbons.

BACKGROUND

Hydrocarbons such as propane, butane, and other alkanes and alkenes are in widespread use, both as fuels and as the precursors for many vital and necessary chemical compounds such as plastics, detergents, pharmaceuticals, etc. Currently the primary sources of these hydrocarbons are fossil fuels, such as natural gas, from which they can be isolated. Such natural sources are, however, only available in limited supply, and retrieval and processing can have undesirable environmental impacts. In addition, the availability and pricing of such fossil fuels is greatly impacted by unpredictable political and social events.

Alternatives sources of such hydrocarbons have been developed, including the so-called Fischer-Tropsch synthesis. One version of this synthesis involves a series of reactions that uses hydrogen gas ($H_2$) to reduce carbon monoxide (CO) in the presence of a metal catalyst (such as cobalt-, nickel-, iron-, or ruthenium-based catalysts) to produce carbon-carbon bond containing alkanes ($C_nH_{(2n+2)}$) and water ($H_2O$). CO can be derived from a number of sources, including waste products of combustion of fossil fuels, natural gas, coal, and biomass. However, the efficiency of this synthesis is relatively low-generally only 25% to 50%. In addition, the process requires elevated temperatures and pressures in order to produce the desired range of alkane products, and careful control of reaction conditions and contaminants in the raw materials is necessary to avoid deactivation of the metal catalyst. As a result, while the Fischer-Tropsch synthesis has been developed for large scale production, it is not in widespread use, due in part to the high costs of reactor construction, operation, and maintenance.

In some instances it has been possible to replace such processes with the use of naturally occurring catalysts (e.g., enzymes) that can catalyze a wide variety of complex reactions at ambient temperatures and pressures, often at high efficiency. For example, monooxygenase enzymes have been used to catalyze oxidation of various hydrocarbons, such as ethylene, in the presence of oxygen to produce, for example, ethanol or ethylene oxide.

In another approach chemoautotrophic microorganisms, which are able to utilize inorganic carbon, are grown in a bioreactor using carbon dioxide ($CO_2$) as a carbon source. Growth of these bacteria provides a biomass that may then be dried and harvested for useful components, for instance lipids and fats can be extracted from dried biomass using solvents and after additional processing may subsequently be used as fuels. Reactor designs are, however, complex in order to accommodate the environmental requirements for chemoautotrophic bacteria. In addition, while this approach does provide reduction of inorganic carbon under relatively mild conditions the resulting product is a highly complex mixture of biomolecules that requires extensive processing in order to isolate useful compounds.

Thus, there is a need for a system and method that can provide reduction of inorganic carbon, such as CO and $CO_2$, to generate hydrocarbons such as alkanes and alkenes under mild conditions.

SUMMARY

In alternative embodiments, provided are nitrogen-fixing, nitrogenase-expressing diazotroph bacteria capable of enzymatically synthesizing hydrocarbons genetically or recombinantly engineered:

to lack or have decreased molybdenum transporter activity, wherein optionally the lack or decreased molybdenum transporter activity is achieved by deletion of one or more, or all, molybdenum transporter genes in the bacteria, or inhibition of molybdenum transporter message (transcript) generation or expression, or inhibition of or decrease in molybdenum transporter protein expression, wherein optionally the molybdenum transporter gene comprises an *Azotobacter vinelandii* modA1, or a molybdenum transporter-periplasmic molybdate-binding protein encoding gene, or a molybdenum ATP-Binding Cassette (ABC) transporter encoding gene, and optionally the molybdenum transporter polypeptide comprises a molybdenum ATP-Binding Cassette (ABC) transporter protein, and optionally the nitrogen-fixing, nitrogenase-expressing diazotroph bacteria comprise bacteria of the family Pseudomonadaceae, or the genus *Azotobacter*, or *Azotobacter vinelandii*, and optionally the nitrogenase comprises a vanadium nitrogenase, or an *Azotobacter* vanadium nitrogenase or an *Azotobacter vinelandii* vanadium nitrogenase.

In alternative embodiments, the bacteria are genetically or recombinantly engineered to express an exogenous nitrogenase, to express more endogenous nitrogenase, or to have increased nitrogenase activity, or any combination thereof, and optionally the exogenous or endogenous nitrogenase comprises a vanadium nitrogenase, or an *Azotobacter* vanadium nitrogenase or an *Azotobacter vinelandii* vanadium nitrogenase, and optionally the exogenous nitrogenase and/or endogenous nitrogenase is modified (e.g., by site-directed or oligonucleotide-directed mutagenesis (including cassette mutagenesis, PCR site-directed mutagenesis, Cre-Lox recombination and whole plasmid mutagenesis), site-specific recombination, or mutagenesis in vivo or in vitro): to have increased enzymatic activity or velocity (Vmax); to be resistant to inhibition by ammonia; to have an enlarged active site to allow the formation of larger hydrocarbons or to allow the formation of larger hydrocarbons at higher efficiency; or, any combination thereof, and optionally the exogenous nitrogenase comprises an affinity tag, wherein optionally the affinity tag comprises: a CREB binding protein (CBP); an avidin or a streptavidin, a biotin or a desthiobiotin, a maltose binding protein (MBP); a glutathione-S-transferase (GST); a poly(His) tag; polyanionic amino acids; a FLAG-tag; or, any combination thereof.

In alternative embodiments, the nitrogen-fixing, nitrogenase-expressing diazotroph bacteria as provided herein can further comprise, or be constructed or engineered to have, deletion of or decreasing the activity of a gene or genes involved in the inhibition of nitrogenase by ammonia, wherein optionally the gene whose activity is deleted or decreased is Nitrogen fixation-L (NifL) (the gene nifL encodes the negative regulator NifL that is expressed in the presence of ammonia; NifL expression can lead to the inhibition of nitrogenase expression), and optionally further comprising overexpressing nifA (enhancement of NifA-mediated transcription by either elimination of nifL or overexpression of nifA can result in ammonium release, correlating with enhanced levels of nifH mRNA, and raised levels of nitrogenase).

In alternative embodiments, provided are methods for making a nitrogen-fixing, nitrogenase-expressing diazotroph bacteria capable of enzymatically synthesizing hydrocarbons, comprising genetically or recombinantly engineering the bacteria to lack or have decreased molybdenum transporter activity, wherein optionally the lack or decreased molybdenum transporter activity is achieved by deletion of one or more, or all, molybdenum transporter genes in the bacteria, or inhibition of molybdenum transporter message (transcript) generation or expression, or inhibition of or decrease in molybdenum transporter protein expression, wherein optionally the molybdenum transporter gene comprises an *Azotobacter vinelandii* modA1, or a molybdenum transporter-periplasmic molybdate-binding protein encoding gene, or a molybdenum ATP-Binding Cassette (ABC) transporter encoding gene, and optionally the molybdenum transporter polypeptide comprises a molybdenum ATP-Binding Cassette (ABC) transporter protein, and optionally the nitrogen-fixing, nitrogenase-expressing diazotroph bacteria comprise bacteria of the family Pseudomonadaceae, or the genus *Azotobacter*, or *Azotobacter vinelandii*, and optionally the nitrogenase comprises a vanadium nitrogenase, or an *Azotobacter* vanadium nitrogenase or an *Azotobacter vinelandii* vanadium nitrogenase.

In alternative embodiments of methods as provided herein, the bacteria are genetically or recombinantly engineered to express an exogenous nitrogenase, to express more endogenous nitrogenase, or to have increased nitrogenase activity, or any combination thereof, wherein optionally the exogenous or endogenous nitrogenase comprises a vanadium nitrogenase, or an *Azotobacter* vanadium nitrogenase or an *Azotobacter vinelandii* vanadium nitrogenase, and optionally the exogenous nitrogenase and/or endogenous nitrogenase is modified (e.g., by site-directed or oligonucleotide-directed mutagenesis (including cassette mutagenesis, PCR site-directed mutagenesis, Cre-Lox recombination and whole plasmid mutagenesis), site-specific recombination, or mutagenesis in vivo or in vitro): to have increased enzymatic activity or velocity (Vmax); to be resistant to inhibition by ammonia; to have an enlarged active site to allow the formation of larger hydrocarbons or to allow the formation of larger hydrocarbons at higher efficiency; or, any combination thereof, and optionally the exogenous nitrogenase comprises an affinity tag, wherein optionally the affinity tag comprises: a CREB binding protein (CBP); an avidin or a streptavidin, a biotin or a desthiobiotin, a maltose binding protein (MBP); a glutathione-S-transferase (GST); a poly(His) tag; polyanionic amino acids; a FLAG-tag; or, any combination thereof.

In alternative embodiments, methods as provided herein further comprise deletion of or decreasing the activity of a gene or genes involved in the inhibition of nitrogenase by ammonia, wherein optionally the gene whose activity is deleted or decreased is Nitrogen fixation-L (NifL), and optionally further comprising overexpressing nifA.

In alternative embodiments, provided are whole cell methods or processes for enzymatically synthesizing hydrocarbons, comprising contacting a nitrogen-fixing, nitrogenase-expressing diazotroph bacteria as provided herein, with a carbon-containing compound under conditions suitable to enzymatically form a carbon-carbon bond-comprising product compound, or a plurality of carbon-carbon bond-comprising product compounds, in the bacteria. In alternative embodiments, the carbon-containing compound comprises: a carbon monoxide (CO); a carbon dioxide ($CO_2$); or a $C_2$, $C_3$, $C_4$, or $C_5$ comprising compound, and optionally the carbon-containing compound is input, or "fed" to the nitrogen-fixing, nitrogenase-expressing diazotroph bacteria as a gas; or, the carbon-carbon bond-comprising product or products comprises or is a $C_2$, $C_3$, $C_4$, or $C_5$ product, or the carbon-carbon bond-comprising product comprises or contains at least one double bond, or the carbon-carbon bond-comprising product or products comprise or are methane, ethane, ethene, propane or butane.

In alternative embodiments of the methods, the contacting comprises conditions comprising high oxygen, low ammonia, or high oxygen and low ammonia. In alternative embodiments of the methods, the nitrogen-fixing, nitrogenase-expressing diazotroph bacteria are cultured, or in a cultured media, or in a bioreactor, and optionally the carbon-containing compound is input or "fed" to the culture, culture media or bioreactor as a gas.

In alternative embodiments, methods as provided herein further comprise harvesting, purifying and/or isolating the carbon-carbon bond-comprising product compound.

In alternative embodiments, provided are bioreactors or fermenters comprising: a culture or a liquid system comprising a nitrogen-fixing, nitrogenase-expressing diazotroph bacteria as provided herein. In alternative embodiments, the bioreactors or fermenters as provided herein further comprise an inlet configured to provide a carbon-containing compound to the culture or liquid system in an amount effective to allow a nitrogenase in the nitrogen-fixing, nitrogenase-expressing diazotroph bacteria produce the carbon-carbon bond-comprising product compound, and optionally further comprising an outlet configured to remove the carbon-carbon bond-comprising product compound.

The details of one or more exemplary embodiments are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

BRIEF DESCRIPTION OF THE DRAWINGS

The drawings set forth herein are illustrative of exemplary embodiments and are not meant to limit the scope of the invention as encompassed by the claims.

FIG. 1 schematically illustrates and exemplary process as provided herein.

Like reference symbols in the various drawings indicate like elements.

Figure 2B:
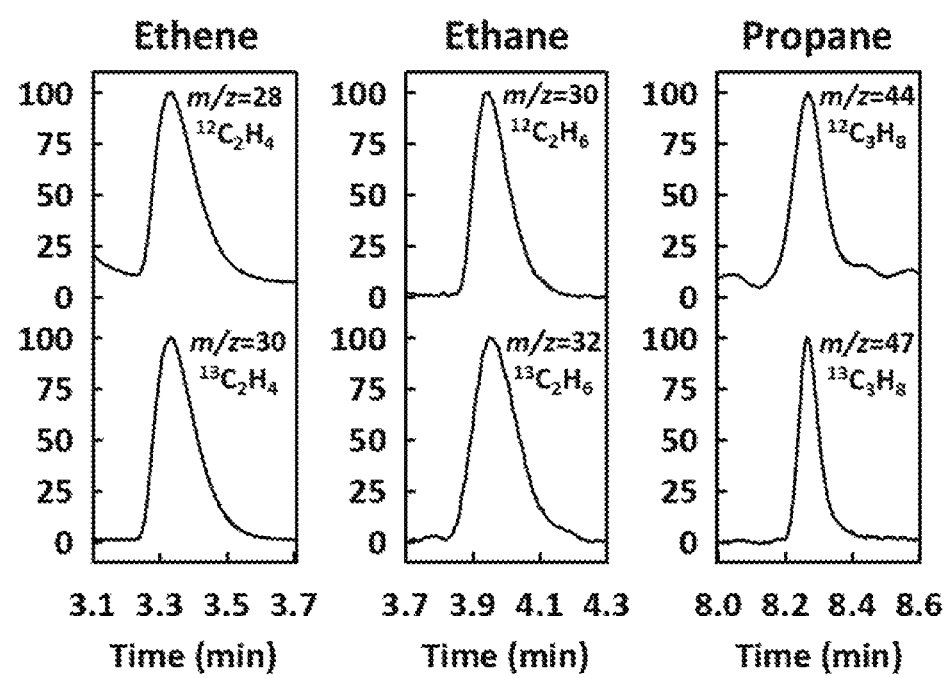
FIG. 2 illustrates in graphic (FIG. 2B) and table form (FIG. 2A) a product analysis of an exemplary method as provided herein by GC-MS analysis. The experiments were performed with naturally-abundant $^{12}CO$ (upper panels) and with isotope-labeled $^{13}CO$ (lower panels) and the masses of products in these experiments were subsequently analyzed by GC-MS. The GC-MS analysis shows that the carbon atoms in the hydrocarbon products originate from the carbon atoms of CO molecules, thereby demonstrating hydrocarbon formation from CO using exemplary genetically modified bacterial cells provided herein, i.e., genetically modified whole cells of *A. vinelandii* that express vanadium nitrogenase.

Reference will now be made in detail to various exemplary embodiments as provided herein, examples of which are illustrated in the accompanying drawings. The following detailed description is provided to give the reader a better understanding of certain details of aspects and embodiments as provided herein, and should not be interpreted as a limitation on the scope of the invention.

DETAILED DESCRIPTION

In alternative embodiments, provided are genetically or recombinantly engineered nitrogen-fixing bacteria capable of enzymatically synthesizing hydrocarbons, and methods for making and using them. In alternative embodiments, provided are genetically or recombinantly engineered nitrogen-fixing bacteria including nitrogen-fixing diazotrophs such as nitrogen-fixing bacteria of the family Pseudomonadaceae, or the genus *Azotobacter*, including *Azotobacter vinelandii*, for the whole cell synthesis of hydrocarbons and carbon-carbon bonds. In alternative embodiments, provided are culture systems and bioreactors using nitrogen-fixing, nitrogenase-expressing bacteria as provided herein for enzymatically synthesizing hydrocarbons.

In alternative embodiments, nitrogen-fixing, nitrogenase-expressing diazotroph bacteria used to practice embodiments as provided herein are genetically or recombinantly engineered to express an exogenous nitrogenase, to express more endogenous nitrogenase, or to have increased nitrogenase activity, or any combination thereof. In alternative embodiments, the exogenous or endogenous nitrogenase comprises a vanadium nitrogenase, or an *Azotobacter* vanadium nitrogenase or an *Azotobacter vinelandii* vanadium nitrogenase. In alternative embodiments, enzymatically active fragments of nitrogenases, e.g., vanadium nitrogenases, are used, e.g., as exogenous sources of nitrogenase enzyme activity. In alternative embodiments, methods and devices (e.g., bioreactors or fermenters) as provided herein employ use or genetically or recombinantly engineered vanadium nitrogenases, vanadium nitrogenase fragments, vanadium nitrogenase isoforms, genetically modified vanadium nitrogenase, and/or metal complexes derived from vanadium nitrogenase alone or in combination to produce hydrocarbons and/or to form carbon-carbon bonds.

Nitrogenases

In alternative embodiments, provided are nitrogen-fixing, nitrogenase-expressing diazotroph bacteria capable of enzymatically synthesizing hydrocarbons genetically or recombinantly engineered to lack or have decreased molybdenum transporter activity. In alternative embodiments, exogenous nitrogenases are added to a bacterial cell to supplement endogenous nitrogenase activity or the provide nitrogenase activity. In alternative embodiments, endogenous and/or exogenous nitrogenases are genetically or recombinantly engineered: to have increased enzymatic activity or velocity (Vmax); to be resistant to inhibition by ammonia; to have an enlarged active site to allow the formation of larger hydrocarbons or to allow the formation of larger hydrocarbons at higher efficiency; or, any combination thereof.

Any nitrogenases can be used to embodiments as provided herein, including vanadium-containing nitrogenases and molybdenum-containing nitrogenases, and nitrogenases not containing these or any metals. For example, in alternative embodiments, nitrogenases used to practice embodiments as provided herein comprise use of an Fe protein, which hydrolyzes ATP to drive the reaction, and a VFe protein, where reaction with a substrate molecule (which in nature is $N_2$) takes place. Nitrogenases used to practice embodiments as provided herein also can contain a number of metal complexes or metal clusters; and the Fe protein can contain an $Fe_4S_4$ iron-sulfur complex, while the VFe protein can contain both an iron-sulfur P cluster near the area of interaction with the Fe protein and a vanadium-iron (VFe) cofactor complex at the active site. Molybdenum containing nitrogenases also can be used to practice embodiments as provided herein, and they have a similar structure but have a molybdenum-iron (MoFe) cofactor complex in place of a VFe cofactor. Nitrogenases containing neither vanadium or molybdenum and utilizing iron-iron (FeFe) cofactors can be used to practice embodiments as provided herein.

In alternative embodiments, mutated forms of nitrogenases used to practice embodiments as provided herein have different forms of these metal complexes and may lack a functional cofactor at the active site. While $N_2$ is the best known substrate for these enzymes, some nitrogenases used to practice embodiments as provided herein exhibit catalytic activities other than reduction of nitrogen. For example, nitrogenases used to practice embodiments as provided herein also comprise enzymes able to convert acetylene into ethylene, carbonyl sulfide into CO and $H_2S$, $CO_2$ into CO and $H_2O$, and $H^+$ into $H_2$. In some embodiments, $H_2$ is a competitive inhibitor, CO is a non-competitive inhibitor, for an exemplary Mo-containing nitrogenase.

Antisense Inhibitory Molecules

In alternative embodiments, provided are nitrogen-fixing, nitrogenase-expressing diazotroph bacteria capable of enzymatically synthesizing hydrocarbons that are genetically or recombinantly engineered to lack or have decreased molybdenum transporter activity.

In alternative embodiments, to decrease molybdenum transporter activity, provided are methods for using antisense inhibitory molecules comprising a sequence used to target either a sense or an antisense strand of a molybdenum transporter activity protein-expressing genes, e.g., such as *Azotobacter vinelandii* modA1, or a molybdenum transporter-periplasmic molybdate-binding protein encoding gene, or a molybdenum ATP-Binding Cassette (ABC) transporter encoding genes or transcripts. Naturally occurring or synthetic nucleic acids can be used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata (1997) Toxicol Appl Pharmacol 144:189-197; Antisense Therapeutics, ed. Agrawal (Humana Press, Totowa, N.J., 1996). Antisense oligonucleotides having synthetic DNA backbone analogues can also include phosphoro-dithioate, methylphosphonate, phosphoramidate, alkyl phosphotriester, sulfamate, 3'-thioacetal, methylene(methylimino), 3'-N-carbamate, and morpholino carbamate nucleic acids, as described above.

RNA Interference (RNAi)

In one aspect, an RNA inhibitory molecule, a so-called "RNAi" molecule, comprising a sequence is used to practice embodiments as provided herein, e.g., a sequence inhibitory to molybdenum transporter activity protein-expressing genes or transcripts. In alternative embodiments, the RNAi molecule comprises a double-stranded RNA (dsRNA) molecule. The RNAi molecule can comprise a double-stranded RNA (dsRNA) molecule, e.g., siRNA, miRNA (micro-RNA), an artificial micro RNA, and/or short hairpin RNA (shRNA) molecules. The RNAi molecule, e.g., siRNA (small inhibitory RNA), miRNA, or an artificial micro RNA, can inhibit expression of a molybdenum transporter activity protein-expressing gene or transcript.

In alternative aspects, the RNAi is about 11, 12, 13, 14, 15, 16, 17, 18, 19, 20, 21, 22, 23, 24, 25 or more duplex nucleotides in length. While the invention is not limited by any particular mechanism of action, the RNAi can enter a cell and cause the degradation of a single-stranded RNA (ssRNA) of similar or identical sequences, including endogenous mRNAs. When a cell is exposed to double-stranded RNA (dsRNA), mRNA from the homologous gene is selectively degraded by a process called RNA interference (RNAi). A possible basic mechanism behind RNAi, e.g., siRNA for inhibiting transcription and/or miRNA to inhibit translation, is the breaking of a double-stranded RNA (dsRNA) matching a specific gene sequence into short pieces called short interfering RNA, which trigger the degradation of mRNA that matches its sequence. In one aspect, the RNAi's are used in gene-silencing therapeutics, see, e.g., Shuey (2002) Drug Discov. Today 7:1040-1046. In one aspect, provided are methods to selectively degrade RNA using the RNAi's. The process may be practiced in vitro, ex vivo or in vivo. In one aspect, the RNAi molecules used to practice embodiments as provided herein generate a loss-of-function mutation (of a molybdenum transporter activity protein-expressing gene or protein) in the bacteria.

In alternative embodiments, intracellular introduction of the RNAi (e.g., miRNA, artificial micro RNA or siRNA) is by internalization of a target cell specific ligand bonded to an RNA binding protein comprising an RNAi (e.g., micro-RNA) is adsorbed. The ligand is specific to a unique target cell surface antigen. The ligand can be spontaneously internalized after binding to the cell surface antigen. If the unique cell surface antigen is not naturally internalized after binding to its ligand, internalization can be promoted by the incorporation of an arginine-rich peptide, or other membrane permeable peptide, into the structure of the ligand or RNA binding protein or attachment of such a peptide to the ligand or RNA binding protein. See, e.g., U.S. Patent App. Pub. Nos. 20060030003; 20060025361; 20060019286; 20060019258. In one aspect, provided are lipid-based formulations for delivering, e.g., introducing nucleic acids as nucleic acid-lipid particles comprising an RNAi molecule to a cell, see e.g., U.S. Patent App. Pub. No. 20060008910.

In alternative embodiments, methods for making and using RNAi molecules, e.g., siRNA, artificial micro RNA and/or miRNA, for selectively degrade RNA include, e.g., U.S. Pat. Nos. 6,506,559; 6,511,824; 6,515,109; 6,489,127.

In alternative embodiments, known and routine methods for making expression constructs, e.g., vectors or plasmids, from which an inhibitory polynucleotide (e.g., a duplex siRNA) is transcribed are used. A regulatory region (e.g., promoter, enhancer, silencer, splice donor, acceptor, etc.) can be used to transcribe an RNA strand or RNA strands of an inhibitory polynucleotide from an expression construct. When making a duplex siRNA (e.g., to molybdenum transporter activity protein-expressing gene) inhibitory molecule, the sense and antisense strands of the targeted portion of the targeted IRES can be transcribed as two separate RNA strands that will anneal together, or as a single RNA strand that will form a hairpin loop and anneal with itself.

For example, in alternative embodiments, a construct targeting a portion of molybdenum transporter activity protein-expressing gene is inserted between two promoters (e.g., two plant, viral, bacteriophage T7 or other promoters) such that transcription occurs bidirectionally and will result in complementary RNA strands that may subsequently anneal to form an inhibitory siRNA. Alternatively, a targeted portion of molybdenum transporter activity protein-expressing gene can be designed as a first and second coding region together on a single expression vector, wherein the first coding region of the targeted gene is in sense orientation relative to its controlling promoter, and wherein the second coding region of the gene is in antisense orientation relative to its controlling promoter. If transcription of the sense and antisense coding regions of the targeted portion of the targeted gene occurs from two separate promoters, the result may be two separate RNA strands that may subsequently anneal to form a gene or inhibitory siRNA, e.g., molybdenum transporter activity protein-expressing gene-inhibitory siRNA used to practice embodiments as provided herein.

In alternative embodiments, transcription of the sense and antisense targeted portion of the targeted nucleic acid, e.g., molybdenum transporter activity protein-expressing gene, is controlled by a single promoter, and the resulting transcript can be a single hairpin RNA strand that is self-complementary, e.g., forms a duplex by folding back on itself to create a (e.g., molybdenum transporter activity protein-expressing gene)-inhibitory siRNA molecule. In this configuration, a spacer, e.g., of nucleotides, between the sense and antisense coding regions of the targeted portion of the targeted (e.g., molybdenum transporter activity protein-expressing) gene can improve the ability of the single strand RNA to form a hairpin loop, wherein the hairpin loop comprises the spacer. In one embodiment, the spacer comprises a length of nucleotides of between about 5 to 50 nucleotides. In one aspect, the sense and antisense coding regions of the siRNA can each be on a separate expression vector and under the control of its own promoter.

Inhibitory Ribozymes

In alternative embodiments, provided are ribozymes capable of binding molybdenum transporter activity protein-expressing genes, coding sequences or messages. These ribozymes can inhibit gene activity by, e.g., targeting mRNA.

Strategies for designing ribozymes and selecting the gene specific antisense sequence for targeting are well described in the scientific and patent literature, and the skilled artisan can design such ribozymes using the reagents and sequences used to practice embodiments as provided herein.

Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it can be released from that RNA to bind and cleave new targets repeatedly.

Bioreactors, Culture Systems, and Fermenters

In alternative embodiments, provided are culture systems, bioreactors and fermenters comprising and comprising use of nitrogen-fixing, nitrogenase-expressing diazotroph bacteria as provided herein, for e.g., enzymatically synthesizing hydrocarbons.

In alternative embodiments, the various devices used to practice embodiments as provided herein (e.g., culture systems, bioreactors and fermenters) comprise an inlet configured to provide a carbon-containing compound to the culture or liquid system in an amount effective to allow a nitrogenase in the nitrogen-fixing, nitrogenase-expressing diazotroph bacteria produce the carbon-carbon bond-comprising product compound. In alternative embodiments, the various devices as provided herein further comprise an outlet configured to remove the carbon-carbon bond-comprising product compound.

In alternative embodiments, the various devices provided herein are manufactured or configured to comprise, culture and/or hold a liquid (e.g., a culture media) with exemplary nitrogen-fixing, nitrogenase-expressing diazotroph bacteria provided herein.

In alternative embodiments, the various devices provided herein are manufactured or configured to comprise an inlet that permits a carbon-containing compound to be introduced into the liquid in at a rate and/or amount that is effective in providing the nitrogenase with sufficient starting material for the formation of a hydrocarbon, i.e., the carbon-carbon bond-comprising product compound. In alternative embodiments, the various devices provided herein are manufactured or configured to comprise an outlet that permits removal of the hydrocarbon product, e.g., the carbon-carbon bond-comprising product compound.

In alternative embodiments, the various devices provided herein are manufactured or configured such the nitrogen-fixing, nitrogenase-expressing diazotroph bacteria provided herein are immobilized on a surface, e.g., a semi-solid or a solid surface, which may be conductive.

In alternative embodiments, devices provided herein, or devices used to practice embodiments of methods provided herein, including exemplary culture systems, bioreactors and fermenters, can be designed based on or comprise components of or can be practiced or used as described by, e.g., U.S. Pat. No. 8,895,291 (describing e.g., closed cell expansion systems); U.S. Pat. No. 8,889,400 (describing e.g., bioreactor systems using gaseous exhausts comprising e.g., carbon monoxide); U.S. Pat. No. 8,865,460 (describing e.g., multi-chambered cell co-culture systems); U.S. Pat. No. 8,852,933 (describing e.g., flexible, deformable, chambers suitable for seeding and growing cells); U.S. Pat. No. 8,852,925 (describing e.g., bioreactors and fermenters comprising three-dimensional matrices, e.g., made of a hydrogel material); U.S. Pat. No. 8,852,923 (describing e.g., tissue conditioning bioreactor modules); U.S. Pat. No. 8,835,159 (describing e.g., static solid state bioreactors); U.S. Pat. No. 8,828,692 (describing e.g., membrane supported bioreactors for conversion of syngas components such as carbon monoxide to liquid products); U.S. Pat. No. 8,518,691 (describing e.g., horizontal array bioreactors for conversion of syngas components to liquid products), and U.S. Pat. No. 8,222,026 (describing e.g., stacked array bioreactors for conversion of syngas components to liquid products).

A number of exemplary embodiments have been described. Nevertheless, it can be understood that various modifications may be made without departing from the spirit and scope of the invention. Accordingly, other embodiments are within the scope of the following claims.

What is claimed is:

1. A whole cell method for recombinantly engineering the enzymatic synthesis of a carbon-carbon bond-comprising product compound in the cell, comprising:
   contacting a nitrogen-fixing, nitrogenase-expressing diazotroph bacteria with an exogenous carbon-containing compound or a plurality of exogenous carbon-carbon-containing compounds under conditions suitable to enzymatically form a carbon-carbon bond-comprising product compound, or a plurality of carbon-carbon bond-comprising product compounds, incorporating the exogenous carbon-containing compound or compounds in the nitrogen-fixing, nitrogenase-expressing diazotroph bacteria,
   wherein the nitrogen-fixing, nitrogenase-expressing diazotroph bacteria is recombinantly engineered to increase hydrocarbon synthesis by decreasing or removing molybdenum transporter activity.

2. The whole cell method of claim 1, wherein the exogenous carbon-containing compound comprises: a carbon monoxide (CO); a carbon dioxide ($CO_2$); a CO and a $CO_2$; a $C_2$, a $C_3$, a $C_4$, or a $C_5$ comprising compound; or a CO and a $CO_2$ and a $C_2$ a $C_3$, a $C_4$, or a $C_5$ comprising compound; or a CO or a $CO_2$ and a $C_2$, a $C_3$, a $C_4$, or a $C_5$ comprising compound, and optionally the exogenous carbon-containing compound is input, or "fed" to the nitrogen-fixing, nitrogenase-expressing diazotroph bacteria as a gas.

3. The whole cell method of claim 1, wherein the carbon-carbon bond-comprising product comprises or is a $C_1$, a $C_2$, a $C_3$, a $C_4$, or a $C_5$ product, or the carbon-carbon bond-comprising product comprises or contains at least one double bond, or the carbon-carbon bond-comprising product or products comprise or are methane, ethane, ethene, propane or butane.

4. The whole cell method of claim 1, wherein the contacting comprises conditions comprising high oxygen, low ammonia, or high oxygen and low ammonia.

5. The whole cell method of claim 1, wherein the nitrogen-fixing, nitrogenase-expressing diazotroph bacteria are cultured, optionally cultured in a cultured media or in a bioreactor, and optionally the carbon-containing compound is input or "fed" to the culture, culture media or bioreactor as a gas.

6. The whole cell method of claim 1, further comprising harvesting, purifying and/or isolating the carbon-carbon bond-comprising product compound.

7. The whole cell method of claim 1, wherein the decreased or removed molybdenum transporter activity is achieved by deletion of one or more, or all, molybdenum transporter genes in the nitrogen-fixing, nitrogenase-expressing diazotroph bacteria, or inhibition of molybdenum transporter message or transcript generation or expression, or inhibition of or decrease in molybdenum transporter protein expression.

8. The whole cell method of claim 1, wherein the molybdenum transporter gene comprises an *Azotobacter vinelandii* molybdenum transporter gene, or the molybdenum transporter protein comprises an *Azotobacter vinelandii* molybdenum transporter protein, and optionally the *Azotobacter vinelandii* molybdenum transporter gene comprises an *Azotobacter vinelandii* modA1 transporter gene.

9. The whole cell method of claim 7, wherein the molybdenum transporter protein comprises a molybdenum ATP-Binding Cassette (ABC) transporter protein.

10. The whole cell method of claim 1, wherein the decreased or removed molybdenum transporter activity is achieved by deletion of a molybdenum transporter-periplasmic molybdate-binding protein encoding gene.

11. The whole cell method of claim 1, wherein the decreased or removed molybdenum transporter activity is achieved by deletion of a molybdenum ATP-Binding Cassette (ABC) transporter encoding gene.

12. The whole cell method of claim 1, wherein the nitrogen-fixing, nitrogenase-expressing diazotroph bacteria are further recombinantly engineered to express:
(a) an exogenous nitrogenase to increase nitrogenase activity in the cell; or
(b) more endogenous nitrogenase to have increased nitrogenase activity in the cell,
and optionally the nitrogenase comprises a vanadium nitrogenase, or an *Azotobacter* vanadium nitrogenase or an *Azotobacter vinelandii* vanadium nitrogenase.

13. The whole cell method of claim 12, wherein the exogenous nitrogenase comprises an affinity tag,
wherein optionally the affinity tag comprises: a CREB binding protein (CBP); an avidin or a streptavidin, a biotin or a desthiobiotin, a maltose binding protein (MBP); a glutathione-S-transferase (GST); a poly(His) tag; polyanionic amino acids; a FLAG-tag; or, any combination thereof.

14. The whole cell method of claim 1, wherein the nitrogen-fixing, nitrogenase-expressing diazotroph bacteria are further recombinantly engineered to delete or decrease the activity of a gene or genes involved in the inhibition of nitrogenase by ammonia, and optionally the gene whose activity is deleted or decreased is a Nitrogen fixation-L (NifL), and optionally further comprising overexpressing nifA.

15. The whole cell method of claim 1, wherein nitrogen-fixing, nitrogenase-expressing diazotroph bacteria comprise a bacterium of the family Pseudomonadaceae.

16. The whole cell method of claim 15, wherein nitrogen-fixing, nitrogenase-expressing diazotroph bacteria of the family Pseudomonadaceae comprise a bacterium of the genus *Azotobacter*, or a bacterium of the genus *Azotobacter vinelandii*.

17. The whole cell method of claim 6, further comprising harvesting and/or isolating the carbon-carbon bond-comprising product compound from an extracellular milieu.

18. The whole cell method of claim 6, further comprising harvesting the carbon-carbon bond-comprising product compound from an outlet of a bioreactors or a fermenter configured to remove the carbon-carbon bond-comprising product compound.

* * * * *